United States Patent [19]
De Heij et al.

[11] Patent Number: 5,296,461
[45] Date of Patent: Mar. 22, 1994

[54] DITERPENOID ALCOHOLS FOR FLAVOURING PURPOSES

[75] Inventors: Johannes T. De Heij, Hilversum; Johannes M. Van Dort, Lage Vuursche; Harrie Renes, Nederhorst den Berg, all of Netherlands

[73] Assignee: Unilever Patent Holdings B.V., Vlaardingen, Netherlands

[21] Appl. No.: 970,869

[22] Filed: Nov. 3, 1992

[30] Foreign Application Priority Data

Nov. 4, 1991 [EP] European Pat. Off. ........ 91202865.1

[51] Int. Cl.$^5$ .............................................. A61K 7/46
[52] U.S. Cl. ......................................... 512/15; 512/1
[58] Field of Search ................... 512/15, 1; 568/821, 568/620

[56] References Cited

FOREIGN PATENT DOCUMENTS 0035684  8/1981  Fed. Rep. of Germany .

OTHER PUBLICATIONS

Klein et al; "Chemical Abstracts", vol. 89(1) 1978 89:6444g.
Bohimann et al "Chemical Abstracts", vol. 94 (19) 1981 94:15702y.
Strappaghetti et al "Chemical Abstracts" vol. 97 (1) 1982 97:6570k.
Kobayashi et al "Chemical Abstracts" vol. 111 (5) 1989 111:36831w.
Olsson et al; Tobacco Chemistry. 72. *Five New Cembratrienetri ols from Tobacco, Acta Chemica Scandinavica 45 (1991), pp. 92-98.
Arndt et al, Tobacco Chemistry.71.*Structure Determination and Biomimetic Studies of Five New Tobacco Cembranoids, Acta Chemical Scandinavica 44 (1990), pp. 814-825.
Tius, Synthesis of Cembranes and Cembranolides, Chemical Reviews, vol. 88, No. 5, Jul./Aug. 1988, pp. 719-732.
Maupetit et al, New Constituents in Olibanum Resinoid and Essential Oil, Perfumer & Flavorist, Dec. 1984/Jan. 1985, vol. 9.
Verghese, Olibanum in Focus, Perfumer & Flavorist, Mar. 1988, vol. 13; Obermann, von Weihrauchharzen, pp. 260-265.
Klein et al, (S)-1-Isopropyl-4,8,12-Trimethyl-Cyclotetradeca-3E,7E,11E-Trien-1-OL, EIN Neues Cembrenol Aus Dem Atherischen Ol Von Olibanum, Tetrahedron Letters No. 4, 1978, pp. 349-352.
Vernin et al GC-MS Data Bank Analysis of the Essential Oils From Boswelia Frereana Birdo and Boswelia Carterii Birdw, pp. 511-542.
Wahlberg et al, Tobacco Isoprenoids, Natural Product Reports, 1987, pp. 237-276.
J. C. Leffingwell et al., 'Tobacco flavoring for smoking products', 1972, R. J. Reynolds, Winston-Salem, N.C., USA, p. 57.
Database WPI, Section Ch, Week 8011, Derwent Publications Ltd., London, GB; Class C04, AN 80-19791C(11) & SU-A-672 209 (Leningrad Forestry Acad) Jul. 8, 1979.
G. Vernin et al., "Flavors and Off-Flavors", Proceedings of the 6th International Flavor Conference, Jul 5-7, 1989, pp. 511-541.
J. Verghese, Pref. & Flav. 13, Mar. 1988, pp. 4-12.

*Primary Examiner*—Werren B. Lone
*Attorney, Agent, or Firm*—Cushman, Darby & Cushman

[57] ABSTRACT

The invention relates to products for flavouring purposes. The products according to the invention can be obtained from vegetable material. By applying an extraction step a fractionation product enriched in diterpenols is obtained. Due to their specific flavour and the fact that some heating is preferred for the most beneficial effect makes that the compounds according to the invention are especially useful for flavouring tobacco, tobacco products and tobacco substitutes of any kind.

13 Claims, No Drawings

DITERPENOID ALCOHOLS FOR FLAVOURING PURPOSES

The invention relates to compounds for flavouring purposes. More specifically, the invention relates to the use of certain diterpenoid alcohols for flavouring tobacco, tobacco products or tobacco substitutes. The invention also relates to a process for obtaining the said compounds from vegetable material.

In EP-A-0 035 684 a process is disclosed for producing tobacco flavour components by photo-oxidation of diterpenes. Mixtures rich in these diterpenes were obtained from extracts of various parts of fresh tobacco plants. Thus obtained diterpenoids were subsequently oxidized by irradiation with UV light in the presence of air or oxygen, whereafter the oxidation products were isolated from the solution using column chromatography. Thus, after extraction of tobacco leaves and subsequent separation, the obtained diterpenes must be subjected to a photo-oxidation and a purification process to obtain compounds suitable for use in tobacco flavouring compositions.

I. Wahlberg and C. R. Enzell (Research Department, Swedish Tobacco Company, Stockholm, Sweden) have reported in a literature review covering the period of 1975-1984 that over 2500 compounds, including many diterpenoids and derivatives thereof, are present in tobacco. Nothing is stated about the organoleptic importance of these diterpenoids.

Diterpenoids have also been found by P. Maupetit (Perfumer & Flavorist, 9, 19-37, 1984/1985) in vegetable material of the genus Boswellieae (fa. Burseraceae). Therein it is disclosed that a gum resin containing over 250 components can be obtained from said vegetable material.

Despite the fact that there is a large number of compounds known for flavouring tobacco, tobacco products and/or tobacco substitutes there is a continuous need for novel flavouring components and compositions, and there is a growing need for flavouring components obtained from a natural source.

It has now been found that products obtained by fractionation of vegetable material derived from plants belonging to the family Burseraceae or the family Pinaceae, which fractionation leads to enrichment of diterpenoid alcohols (and more in particular of cembranoid alcohols), are suitable for flavouring tobacco, tobacco products or tobacco substitutes. Such products are hereinafter referred to as fractionation products. The term enrichment of diterpenoid alcohols is to be understood as referring to a fractionation leading to a product with a higher content of diterpenoid alcohols, and more in particular of cembranoid alcohols, than the vegetable material to be fractionated. Fractionation products should preferably containing at least 2% by weight, more preferably at least 5% by weight, of cembranoid alcohols. Vegetable material derived from plants is herein to be understood to comprise, leaves, roots, bark, stems, as well as excretion products such as resins or resinoid matter.

Of the plants belonging to the family Pinaceae, the genus Abietoideae. (especially its species Pseudotsuga menziezii) and the genus Pinoideae (in particular its species Pinus Koraiensis, Pinus cembra and Pinus cembroides) are preferred to provide the vegetable starting material for the fractionation products. Likewise, from the plants of the family Burseraceae the genus Boswellieae. (especially its species Boswellia), is preferred to provide the vegetable starting material for the fractionation products. The fractionation should be directed so as to reduce the content of undesirable substances, more particularly volatile components and saccharides and saccharide derivatives. Other compounds like resin acids may either be incorporated in the fractionation products or excluded therefrom, as desired. Suitable fractionation processes include extraction and distillation or combinations thereof. The fractionated product should preferably contain less than 5% by weight, more preferably less than 2% by weight, of volatile components, which for the purpose of this invention are defined as compounds having a boiling point below 80° C. at 1 kPa.

It has particularly been found that olibanum is most preferred as raw material for said fractionation. Olibanum is a resinous material obtained from plants of the genus Boswellieae (fam. Burseraceae), and is commercially available in various grades.

Especially useful for flavouring tobacco, tobacco products or tobacco substitutes are fractionation products comprising one or more of the compounds I, II and III having the formulae below.

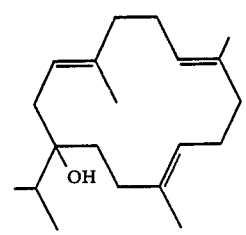

I

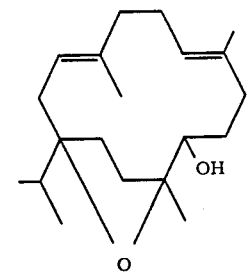

II

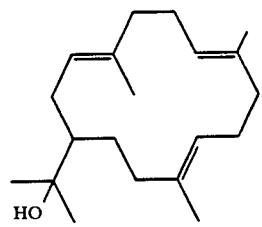

III

Fractionation products comprising one or more of these compounds may be obtained from olibanum. The presence of compounds I and II in some olibanum sources has been reported (H. Obermann, Dragoco Berichte; E. Klein, H. Obermann Tetrah. Letters, pp 349-352, 1978) however, without any indication of organoleptic properties.

Suitable fractionation methods for obtaining such fractionation products include distillation, particularly distillation under reduced pressure or steam distillation. Such distillation may be combined with extraction with an organic solvent, e.g. an alcohol such as ethanol, or a hydrocarbon such as hexane or cyclohexane, depending on the quality of the starting material and the desired composition of the ultimate fractionation product.

If desired, the fractionation may be continued, and may include other fractionation processes than those referred to above, such as various forms of chromatography, until the compounds I, II and III are obtained in a substantially pure form. Alternatively, one or more of the compounds I, II and III may be obtained from other sources or via synthesis.

For the purposes of this invention all such products, including substantially pure forms of the compounds I, II and III will be considered to be comprised in the term "fractionation products". Preferred fractionation products contain at least 0.2% by weight, more preferably at least 0.5% by weight of compound III.

The fractionation products according to the invention can be used as such, in admixture with each other, or as part of a flavouring composition. In the latter case the flavouring composition comprises compounds usually present in such a composition and a fractionation product according to the invention. In this connection the term "flavouring composition" is defined as a mixture of flavouring components, if desired dissolved in a suitable solvent or mixed with a powdered substrate or processed to form a powdered product, which is intended to provide a flavour to a product or to change, enhance or improve the flavour such product already has. Such flavouring compositions may also include flavour precursor systems.

The quantities of the fractionation products to be used may be strongly divergent and depend, inter alia, on the tobacco product in which the compounds are used, on the nature and the quantity of the other components present in a flavouring composition and on the desired flavour effect. In such compositions an amount of 0.01% or more of the fractionation products will generally have a clearly perceptible organoleptic effect. The amount of fractionation products present in end products will generally be 0.01 ppm or more.

Although the fractionation products are suitable to impart a flavour to a number of products, it is preferred that the flavoured products are heated in some stage of their use, because the fractionation products according to the invention as such are not very volatile under ambient conditions. This, and their specific flavour potential makes the fractionation products especially suitable for flavouring tobacco, tobacco products and/or tobacco substitutes or materials used for the manufacturing of tobacco products such as e.g. cigarette wrappers. The term "tobacco" will be understood herein to mean natural products such as, for example, Virginia, Burley, Turkish, Maryland, flue-cured and other tobacco types including tobacco-like or tobacco-based products such as reconstituted or homogenized tobacco or leaf and the like. In this connection "tobacco products" mean tobacco or tobacco substitute containing products designed, intended or used for smoking, such as, inter alia, cigarettes, cigars and pipe tobacco. The term "tobacco substitutes" is to be understood herein to be compounds, compositions, materials or structures intended to replace natural tobacco or tobacco products.

Basic flavouring substances which can be advantageously combined with the fractionation products are, for example, natural products such as extracts, essential oils, absolutes, resinoids, resins, concretes etc., but also synthetic basic substances such as hydrocarbons, alcohols, aldehydes, ketones, ethers, acids, esters, acetals, ketals, etc., including saturated and unsaturated compounds, aliphatic, carbocyclic and heterocyclic compounds. Such basic materials are mentioned, for example, in S. Arctander, Perfume and Flavor Chemicals (Montclair, N.J., 1969), in S. Arctander, Perfume and Flavor Materials of Natural Origin (Elizabeth, N.J., 1960), in T. E. Furia et al., CRC Fenaroli's Handbook of Flavor Ingredients, 2nd edition (Cleveland, CRC Press Inc., 1983, H. B. Heath, Source Book of Flavours, The Avi Publishing Co. Inc. Westport, Conn. (1981) and "Flavor and Fragrance Materials—1991" Allured Publishing Co. Wheaton, Ill. USA.

Auxiliary substances and solvents which can be used in flavouring compositions which comprise fractionation products according to the invention are, for example: ethanol, isopropanol, diethyleneglycol monoethyl ether, glycerol, triacetin etc. The quantities of the fractionation products to be used in a flavouring composition may be strongly divergent and depend, inter alia, on the product wherein the composition is used and on the nature and the quantity of the other components of a flavouring or perfume composition.

A number of ways are possible for applying the fractionation products (either as such or as a part of a composition) to tobacco products or tobacco substitutes, strongly depending on the specific nature of the product or substitute.

In the case of tobacco, methods for applying flavours or flavouring compositions are known in the art and include simply spraying or atomizing the flavour or flavouring composition (sometimes diluted with a suitable solvent like alcohol) over the bulk of the tobacco. Another method may be finely dispersing an emulsion over the bulk of the tobacco, wherein the emulsion comprises an emulsifier, an aqueous phase, and an oil phase, which may comprise fractionation products according to the invention. Other compounds may be included in the formulation. Such a method is described in more detail in EP-A-366 835. Still another method for applying the flavour compounds to the tobacco is a method in which the flavour components (optionally mixed with other components) are micro-encapsulated and subsequently mixed with the tobacco bulk. Optionally an adhesive may be used to fix the micro-capsules to the tobacco leafs. Thus, tobacco, tobacco products or tobacco substitutes flavoured with the fractionation products according to the invention, either as such or as a part of a composition, can be obtained.

The following examples serve to illustrate the invention, but the invention is in no way limited to these examples.

EXAMPLE 1

After steam distilling olibanum a resinous residue was obtained. 1 kg of this residue was crushed to small pieces, and 1.25 l hexane was added. After stirring, the mixture was kept overnight, during which the major part of the resinoid dissolved. The undissolved matter was filtered off using a Buchner funnel. The volume of the clear liquid was reduced to about a third by partly removing the hexane, using a rotating film evaporator (Rotavap). Distillation at a temperature between 120° and 175° C. (at a pressure of 0.93 kPa) yielded 95 g distillate having a content of about 50% of a mixture of compounds I, II and III.

EXAMPLE 2

A flavour composition for improving the flavour of Burley tobacco was prepared by mixing the following components in amounts as specified (in parts by weight on a total of 1000):

| | |
|---|---|
| Cyclotene | 10 |
| 5-(2-Hydroxyethyl)-4-methylthiazole | 1 |
| 2,3-pentanedione | 2 |
| 2,5-Dimethylpyrazine | 2 |
| Furfurylidene acetone | 2 |
| Furfurylmercaptane solution (10% in ethanol) | 2 |
| Tetramethylpyrazine | 6 |
| Trimethylpyrazine | 10 |
| Maltol solution (10% in ethanol) | 13 |
| 3-Ethyl-pyridine | 25 |
| Cocoa oleoresin | 250 |
| Coffee extract | 300 |
| mixture obtained according to example 1 | 3 |
| Propylene glycol | 374 |

We claim:

1. A composition comprising at least 0.2% by weight of one or more of the compounds I, II and III, wherein said composition contains less than 5% by weight of volatile compounds having a boiling point below 80° C. at 1 kPa, and wherein said compounds I, II and III have the formulas

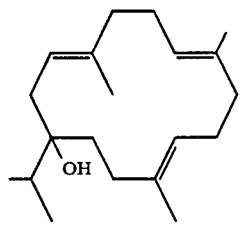

I

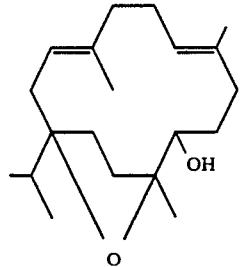

II

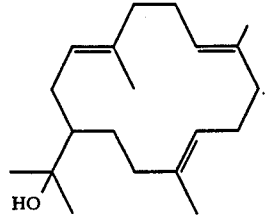

III

2. A composition according to claim 8, which is obtained from vegetable material of plants belonging to the genus Boswellieae (fam. Burseraceae) or to the genus Abietoideae or to the genus Pinoideae (both fam. Pinaceae).

3. A composition according to claim 2, which is obtained from vegetable material of plants belonging to the species Boswellia (genus Boswellieae, fam. Burseraceae).

4. A composition according to claim 3 wherein the vegetable material is olibanum.

5. A composition according to claim 1 which contains less than 5% by weight of volatile components.

6. A composition according to claim 1 comprising at least two of compounds I, II and III and at least 0.2% by weight of compound III.

7. A composition according to claim 6 which comprises at least 5% by weight of cembranoid alcohols.

8. A composition according to claim 1 which is obtained from vegetable material of plants belonging to the family of Burseraceae or Pinaceae.

9. A process for obtaining a composition according to claim 1, which comprises a distillation step.

10. A process according to claim 9, wherein the distillation is carried out under reduced pressure.

11. A flavoring composition for flavoring tobacco, tobacco products or tobacco substitutes, wherein the flavoring composition comprises a composition according to claim 1.

12. Tobacco, tobacco products and tobacco substitutes, which comprise a composition according to claim 1 or claim 11.

13. A process for flavoring tobacco, tobacco products and tobacco substitutes, comprising the step of adding a composition according to claim 1 or claim 12.

* * * * *

UNITED STATES PATENT AND TRADEMARK OFFICE
CERTIFICATE OF CORRECTION

PATENT NO. : 5,296,461
DATED : March 22, 1994
INVENTOR(S) : DE HEIJ et al.

It is certified that error appears in the above-indentified patent and that said Letters Patent is hereby corrected as shown below:

Claim 13, column 6, line 58 (last line), change "12" to --11--.

Signed and Sealed this

Eighteenth Day of October, 1994

Attest:

BRUCE LEHMAN

*Attesting Officer*      *Commissioner of Patents and Trademarks*